United States Patent [19]

Chong et al.

[11] Patent Number: 4,913,136

[45] Date of Patent: Apr. 3, 1990

[54] HARNESS FOR THE TREATMENT OF CONGENITAL HIP DISLOCATION IN INFANTS

[76] Inventors: Andrew K. Chong; Catherine S. Chong, both of 1632 Hemstock Ave., Wheaton, Ill. 60187

[21] Appl. No.: 227,603

[22] Filed: Aug. 2, 1988

[51] Int. Cl.$^4$ ............................................. A61F 3/00
[52] U.S. Cl. ................................. 128/80 A; 128/80 R
[58] Field of Search ............... 128/80 A, 78, 80 B, 128/80 J, 80 R, 80 H

[56] References Cited

U.S. PATENT DOCUMENTS

| | | | |
|---|---|---|---|
| 507,775 | 10/1893 | Bayer | 128/80 B |
| 3,114,368 | 12/1963 | Richmond | 128/80 A |
| 3,730,177 | 5/1973 | Thurm | 128/80 A |
| 3,815,589 | 6/1974 | Bosley | 128/80 A |
| 3,834,376 | 9/1974 | Thurm | 128/80 A |
| 4,108,168 | 8/1978 | Craig | 128/80 A |
| 4,497,315 | 2/1985 | Fettwei et al. | 128/78 |
| 4,543,948 | 10/1985 | Phillips | 128/80 A |
| 4,574,790 | 3/1986 | Wellershaus | 128/78 |

FOREIGN PATENT DOCUMENTS

| | | | |
|---|---|---|---|
| 404473 | 3/1974 | U.S.S.R. | 128/80 J |
| 770488 | 10/1980 | U.S.S.R. | 128/80 R |

*Primary Examiner*—Edgar S. Burr
*Assistant Examiner*—Huong Q. Pham

[57] ABSTRACT

A method of making a harness that significantly facilitates application and enhances its effectiveness in infants with congenital hip dislocation. The novel and significant features of the invention include adjustable attachment of the leg straps at the legs just below the knees and not at the chest, use of an attached toe-cover to prevent slippage of the foot from the stirrup, and color-coding of the leg straps to prevent wrong attachments.

2 Claims, 2 Drawing Sheets

HARNESS FOR THE TREATMENT OF CONGENITAL HIP DISLOCATION IN INFANTS

BACKGROUND OF THE INVENTION

The Pavlik harness was developed in Europe in 1944, and introduced into the United States in 1959. Since then, it has gained in popularity as an effective treatment modality for Congenital Dislocation of the Hip in infants. The Pavlik harness consists of a Chest Halter made up of a belt around the chest, held in place by two shoulder straps, and two foot attachments, each connected to the Chest Halter by an anterior and a posterior leg strap. Traditionally, the buckles for adjustable attachment of the leg straps are on the chest belt. For example, Mubarak in his important paper on the Pavlik Harness published in the Journal of Bone and Joint Surgery (Vol. 63A, No. 8, Oct. 1981) taught that "the buckles for the anterior (flexor) stirrup straps should be located at the child's anterior axilliary line", that is, on the front of the chest. He also taught that "the buckles for the posterior (abduction) stirrup straps should be located over the scapula" or shoulder blade in the back of the chest. With the Chest Halter held securely in place, and adjusting the lengths of the anterior and posterior leg straps, the hip joint can be placed and held in the optimal position for hip stabilisation. This is usually in the position of flexion and abduction. The anterior leg strap limits hip extension and thereby holds the hip in flexion. The posterior leg strap limits hip abduction and thereby holds the hip in abduction. By adjusting the lengths of the anterior and posterior straps, the physician can control the amount of flexion and abduction, holding the hips in optimal position for correction of the hips. The biggest advantage of the Pavlik harness over other forms of splinting is that it allows for controlled motion of the hips during the course of treatment, thus allowing for more normal articular cartilage nutrition and growth.

There are distinct disadvantages however, and they are as follows.

1. The Pavlik harness is notoriously difficult to apply. The Harness as it is presently available consists of a chest halter that has six large metal safety buckles to which the shoulder straps and leg straps are attached. Once the straps are fastened and locked in place, if the position is not optimal, unfastening and refastening is a chore, especially since there are six straps involved (two from the shoulders and four from both legs). A crying wrigglingly infant does not make it any easier. Moreover, the shoulder straps and anterior leg straps are applied with the infant supine (on his back) while the posterior leg straps are applied with the infant prone (on his stomach). During adjustment, it is not uncommon to have to flip the crying infant several times to achieve optimal position.

2. The large metal safety buckles on both the front and back of the chest halter makes lying on it very uncomfortable for the infant.

3. Once the harness has been applied, another problem that often arises is the foot escaping from the foot stirrup. Because the heel of the infant is so small, it is easy for the infant to kick the foot forward, slipping away from the stirrup and nullifying the effect of the Pavlik harness. During the course of treatment, the parents have always to be vigilant, making sure that the foot is replaced on the stirrup every time the infants kicks his foot free from the stirrup.

4. Yet another problem that arises during the course of treatment is attachment of the strap to the wrong buckle on the chest halter. Parents after washing the baby at home and replacing the harness not uncommonly attach the strap to the wrong buckles on the chest halter. This not only frustrates treatment, but may also cause damage to the child's hips. One common problem is for the parent to attach the anterior leg strap to the posterior buckle and vice versa, causing the leg to be held in the abnormal internally rotated position (rather than the desired external rotation) potentially harmful to the child's hips.

BRIEF SUMMARY OF THE INVENTION

The objective of the present invention is to make certain utility improvement in the Pavlik harness to overcome the serious problems enumerated above. The large cumbersome and hard-to-use safety buckles can be replaced by more convenient and less obtrusive devices like hook and loop fasteners (like VELCRO) and the newer plastic buckles and fasteners. This is common knowledge.

But more significant in terms of novelty and utility with the present invention, the lengths of the leg strap are adjusted at the legs just below the knees rather than at the chest halter (as presently available). The anterior leg straps are first adjusted for optimal flexion and then attached with the infant in the supine position. The posterior leg straps are then adjusted for optimal abduction and then attached with the infant also in the supine position. The position of the hips are now checked, and if needed, adjustments to the straps could be made with the infant in the same supine position. There is no need to flip the infant supine and prone repeatedly during adjustment of the straps.

To prevent the foot from slipping out of the foot stirrup, a toe cover (sock) sewn on to the foot stirrup is used. The heel is left exposed, since the foot has a tendency to slip forwards but not backwards.

To prevent mix-up and wrong attachments of the leg straps, the leg straps are color-coded.

DETAILED DESCRIPTION OF THE INVENTION

Figure 1:
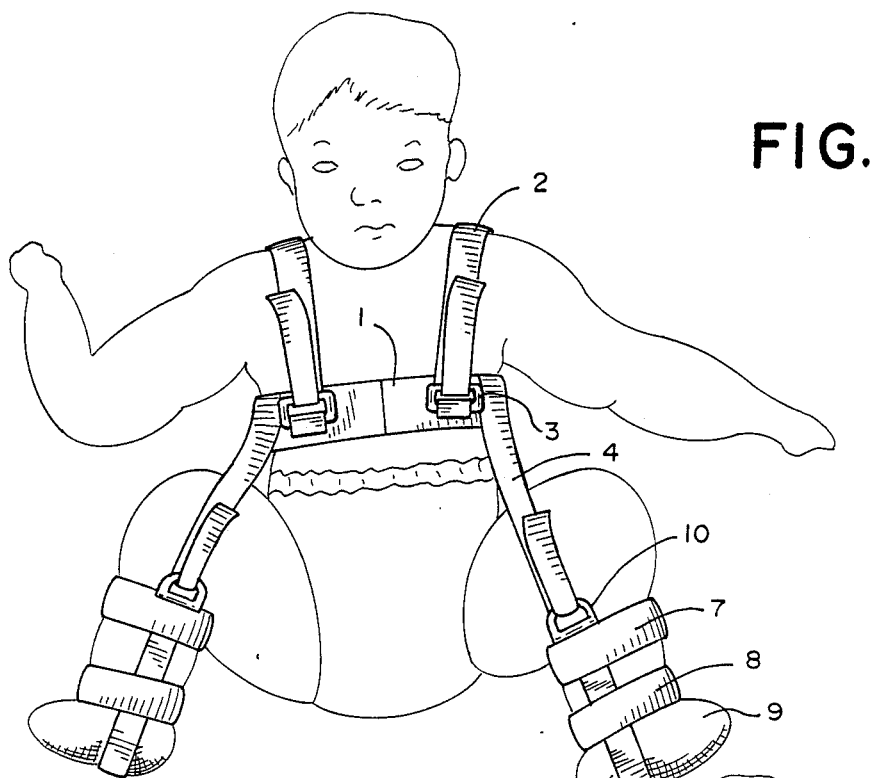
FIG. 1 is a perspective view of the invention in use with the infant supine.
Figure 2:
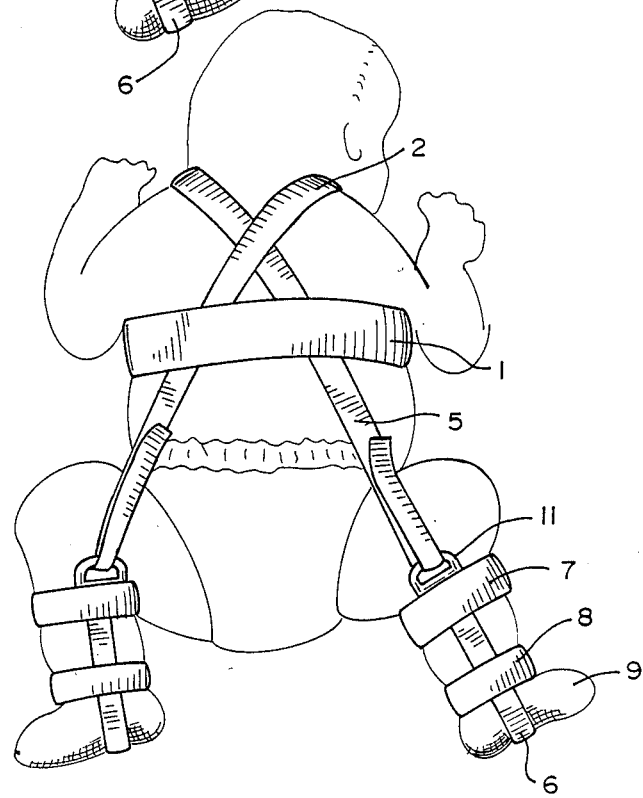
FIG. 2 is a perspective view of the invention in use with the infant prone.

Referring to FIG. 1 and 2, the Chest Halter is constructed of a padded chest belt 1, and shoulder strap 2 crossed at the back to prevent slipping and attached to the chest belt 1 in front using hook and loop fastened around D-rings, or any other kind of fastener 3. Leg straps 4 and 5, two for each leg are sewn onto the chest belt 1. The anterior strap for each leg 4 is sewn on permanently at the anterior axillary line. The posterior strap for each leg 5 is sewn on permanently at the level of the scapula or shoulder blade.

Figure 3A:
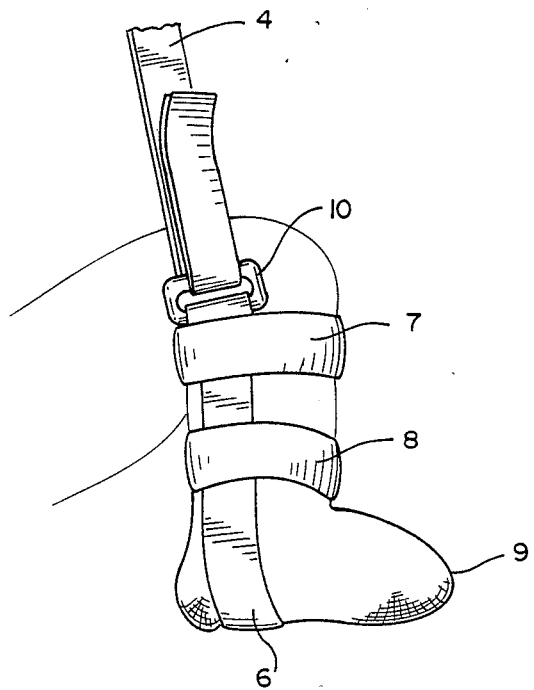
FIG. 3A is a close-up view of the stirrup and footpiece where hook and loop fastened (like VELCRO) is used.
Figure 3B:
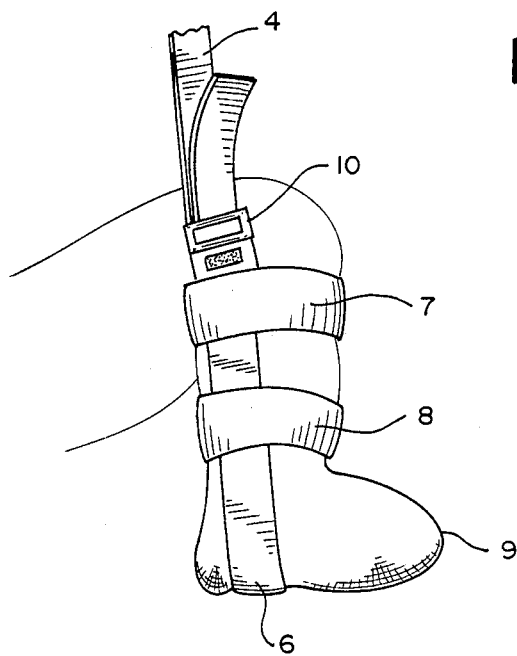
FIG. 3B is a close-up view of the stirup and footpiece where a buckle fasteners is used.

Referring to FIGS. 3A and 3B, the bootie on each leg and foot consists of a foot stirrup 6 that extends around the sole of the foot and extends up the leg to just below the knee both anteriorly and posteriorly. Two VELCRO straps 7 and 8 around the upper and lower parts of the leg keep the stirrup around the leg. A toe-cover 9 (sock) is sewn around the anterior opening at the lower end of the stirrup to keep the foot in position on the stirrup, preventing it from slipping forward. Buckles or D-rings 10 and 11 are sewn onto the upper end of the bootie just below the knee both anteriorly and posteriorly, to be used for attachment of the leg straps 4 and 5 from the chest belt 1.

Color coding is used so that the anterior strap of each leg 4 is attached approximately to the anterior buckle or D-ring 10 (if VELCRO is used) of the corresponding bootie, and the posterior leg strap 5 is also thus appropriately attached to the posterior buckle or D-ring 11. The color coding could be on the buckle or strap or any variation thereof.

Application of the invention thus consists of first attaching the chest belt 1 and the shoulder strap 2, then each bootie in turn, and finally attaching the bootie to the halter by first adjusting the length of the anterior leg strap 4 to hold the hip in optimal flexion, then adjusting the length of the posterior leg strap 5 to hold the hip in optimal abduction. All the steps are done with the infant in the supine position, and there if no need to flip or turn the infant to any other position. This is a significant advantage over the currently available harnesses, where the buckles and hence the adjustments of the leg straps are made at the chest belt. This necessitated turning the patient to the prone position when adjusting the posterior leg straps. Moreover, with the infant prone, the hips by virtue of the prone position, are necessarily in maximum abduction, so that it is difficult to know exactly how much abduction to set the strap at. ("Just enough, but not too much" as advised). Repeated turning of the patient from supine to prone is not uncommon during application, making use of the current Pavlik harness difficult and cumbersome. The invention obviates this difficulty completely.

Color coding guides both the physician and the parent during application of the harness. This is especially important for the parent at home, without the guidance of the physician or nurse at the office. Wrong attachment of the leg straps not only renders the harness ineffective, but can be potentially harmful. For instance, if the anterior strap 4 is attached to the posterior buckle 11 and the posterior strap 5 is attached to the anterior buckle 10, the leg will be twisted into internal rotation, a potentially harmful position for an infant with congenital hip dislocation.

I claim:

1. A harness for the treatment of congenital hip dislocation in infants, comprising
    a chest halter including a belt around the chest, said belt being held in place by two shoulder straps connected to said belt and
    two foot attachments, a posterior and an anterior leg strap connected to each of said foot attachments including adjustment means in each of said leg straps, said adjustment means being located at the point of connection of said leg straps to said foot attachments, each of said foot attachments including a stirrup and a toe-cover attached to the front of each stirrup to prevent foot slippage.

2. The Harness of claim 1, where the leg straps are color-coded for easy identification.

* * * * *